United States Patent [19]

Louderback et al.

[11] Patent Number: 4,677,075

[45] Date of Patent: Jun. 30, 1987

[54] UROBILINOGEN CONTROL

[76] Inventors: Allan L. Louderback, 9661 Longden Ave., Temple City, Calif. 91780; Paul R. Szatkowski, 24 Winthrop Rd., Bethel, Conn. 06801

[21] Appl. No.: 859,339

[22] Filed: May 5, 1986

[51] Int. Cl.[4] ............................................. G01N 31/00
[52] U.S. Cl. ......................................... 436/12; 436/8; 436/18
[58] Field of Search ........................ 436/8–18, 436/44, 63, 96–99; 422/56; 514/55, 167, 330

[56] References Cited

U.S. PATENT DOCUMENTS

| 4,038,485 | 7/1977 | Johnston et al. | 422/56 |
| 4,121,905 | 10/1978 | Maurukas | 436/12 |
| 4,189,401 | 2/1980 | Louderback | 252/408 |
| 4,201,694 | 5/1980 | Louderback | 252/408 |
| 4,279,775 | 7/1981 | Louderback et al. | 436/11 |
| 4,363,801 | 12/1982 | Nagyvary | 514/55 |
| 4,382,062 | 5/1983 | Kohl | 422/56 |
| 4,402,975 | 9/1983 | Takeshita et al. | 514/330 |
| 4,442,093 | 4/1984 | Maeda et al. | 514/167 |
| 4,539,182 | 9/1985 | Johnson et al. | 436/44 |
| 4,551,428 | 11/1985 | Berger et al. | 436/63 |

Primary Examiner—Deborah L. Kyle
Assistant Examiner—T. J. Wallen

[57] ABSTRACT

A stable control solution is provided for the determination of urobilinogen. The control solution comprises an aqueous solution of about 3–12% ethylene glycol, about 0.1% protein and preferably about 40–400 mg/dl urobilinogen, said composition buffered to pH about 8.0–9.0 and retained in a hermetically sealed container under a blanket of inert gas.

7 Claims, No Drawings

UROBILINOGEN CONTROL

BACKGROUND OF THE INVENTION

This invention relates to a stable control solution for the determination of urobilinogen.

Urobilinogen is a reduction product of bilirubin which, in turn, is a breakdown product of heme. The latter substance is formed primarily from the degradation of the red blood cells (erythrocytes). The red blood cells contain hemoglobin which captures and holds oxygen for transfer to all the cells of the body. Hemoglobin also binds in a different way some of the carbon dioxide made in the body. The carbon dioxide is vented out in the lungs when the red blood cells pick up a new amount of oxygen for redistribution to the body.

The red blood cells are made in the bone marrow and since they have no nuclei they have a finite life of usefulness in the body. The average life of a red blood cell is about 120 days. At the end of this time, tne reticuloendothelial (RE) cells in the liver proceed to engulf and destroy the old red blood cells whereby hemoglobin is released into the environment of the RE cells.

The hemoglobin molecule consists of the red heme pigment and a protein called globin. The heme pigment is made up of iron and a cyclic tetrapyrrole known as porphyrin. The porphyrin ring opens up by enzymatic action and forms a green pigment referred to as biliverdin which is then further reduced by enzymatic action to bilirubin.

Both bilirubin and biliverdin are excreted into the bile ducts, and the bile, in turn, is excreted into the intestines. Some of the bile is adsorbed further down in the small intestine and back into the blood stream. The material adsorbed into the blood stream is further reduced to urobilinogen. Part of this adsorbed material then passes out of the body through the kidneys into the urine as urobilinogen or in an oxidized form as urobilin.

Normally, little or no urobilinogen or bilirubin is excreted in the urine unless a pathological condition exists in the liver such as an impairment of the liver cell mechanisms giving rise to various types of jaundice. Urobilinogen problems are more evident with Orientals and the type of liver damage that they can have than with Caucasians. The determination of urinary urobilinogen also is a useful test for detecting the early stages of hepatitis.

In view of the above, determination of urobilinogen in urine is important in clinical testing and diagnostics. Various so-called reagent strips and dipsticks used for urine testing contain tests for urobilinogen. The commercially available Chemstrip ® of Bio-Dynamics, Division Boehringer Mannheim Corp., Indianapolis, Ind., and the N-Multistix ® of Ames Division, Miles Laboratories, Inc., Elkhart, Ind., are typical examples of such products which include tests for urobilinogen.

The classical test, originally devised by Paul Ehrlich in 1901, employs paradimethylaminobenzaldehyde as a test for urobilinogen which in strongly acid medium produces a brown-orange color with said reagent (Ehrlich's reagent). In modifications of this test, 4-methoxybenzene - diazonium - tetrafluoroborate and related compounds replace Ehrlich's reagent as first described by Kutter et al., *Dtsch. Med. Wschr.* 98, 112 (1973).

Further background on urobilinogen and its testing can be had by reference to a common text in the field, for example, Tietz, *Fundamentals of Clinical Chemistry*, W. B. Saunders Company, Philadelphia, Pa., 1970, pp. 762-766. See also, Jackson and Conrad, *Amer. Clin. Prod. Rev.* 4 (12), 10-19 (1985).

As part of normal quality control, the clinician and laboratory technologist must be assured that the urobilinogen test is working properly; that is, it must give a good positive test if positive material is present in the patient's sample. Otherwise, the clinician could miss a potential problem present in the urine which may be indicative of certain liver malfunctions. Availability of a stable control solution for urobilinogen would this find significant use as an adjunct to the quality control of urobilinogen tests.

DESCRIPTION OF THE INVENTION

In accordance with the present invention a stable control solution is provided for the determination of urobilinogen. This control solution can be conveniently added to conventional control media presently used in urine testing, for example, fresh urine, reconstituted urine from a lyophilized state or synthetic urine media, to improve the accuracy and reliability of said media in the quality assurance of urobilinogen testing.

The control solution of this invention comprises a uniquely prepared urobilinogen composition stabilized in about 3-12% ethylene glycol and a small but effective amount of about 0.1% protein buffered to a pH of from about 8.0 to about 9.0 and in which the amount of urobilinogen is sufficient to develop upon dilution in use an activity of from about 0.1 to about 20 mg/dl, said composition being retained in a hermetically sealed container under a blanket of inert gas.

Preferably, the concentration of the ethylene glycol is about 8.0%, the pH is from about 8.2 to about 8.4, the protein is albumin, and the inert gas is nitrogen. The amount of protein should be sufficient to bind the urobilinogen without interfering with any protein testing that may also be desired with the urine sample.

Prior to sealing, dissolved oxygen or air should be expelled from the product which is then exposed to the inert gas blanket. The container preferably is an amber glass ampule or vessel such as to exclude light which may tend to deteriorate the urobilinogen.

The control solution of this invention is prepared by converting bilirubin to urobilinogen with about 5.4% sodium amalgam (NaHg++) in the presence of about 2-7% diethylamine, dissolving the resulting urobilinogen product at a concentration of from about 1% to about 5% urobilinogen in aqueous ethylene glycol at a concentration of from about 3% to about 12% glycol, adding a small but effective amount of about 0.1% protein and adjusting the pH to a level of from about 8.0 to about 9.0.

The control solution is conveniently made in two steps by first preparing a concentrated solution of the urobilinogen and then diluting the same with a diluent solution. Thus, the urobilinogen can be first concentrated in about 15-60% ethylene glycol and about 25% diethylamine. HCl and then diluted with an aqueous diluent solution containing about 0-5% ethylene glycol to reduce the glycol concentration to about 3-12%.

Although control solutions of bilirubin with 15-60% ethylene glycol have been described in U.S. Pat. Nos. 4,189,401 and 4,201,694, it has not been known heretofore to stabilize urobilinogen control solutions with 3-12% ethylene glycol in combination with a small amount of protein as described herein.

It is also preferable to incorporate in the control solution of this invention a small but effective amount of a sulfhydryl or thiol compound such as, for example, dithiothreitol (DTT), dithioerythritol (DTE), 2-mercaptoethanol, glutathione or thiodiglycolic acid. The sulfhydryl compound can be added to the final composition in the ampule to use up any dissolved oxygen remaining in the product which may otherwise react with the urobilinogen.

Small but effective amounts of other additives such as sequestering agents, antifungals and antibiotics can also be incorporated in the final product. Such desired additives can be, for example, disodium ethylenediaminetetraacetic acid (EDTA) to sequester metals and prevent oxidation of the product, fungizone antifungal and Vancomycin and/or Gentimycin antibiotics.

The control solution of this invention has been found to remain stable for periods of time up to 18 months when stored in amber colored ampules at 5° C. In use, the control solution can be conveniently emptied into conventional urine control media in any desired amount. Preferably, about one ml of the control solution is admixed with about 30 ml of the urine control media to give a 1.31 dilution. For example, an ampule concentration of urobilinogen of 124–248 mg/dl when thus diluted for use will give a desired 4–8 mg/dl concentration for the end user testing.

As an example of such end user testing, the urobilinogen control solution of this invention has been used as an additive to reconstituted Kova ® Trol 1, which is a high abnormal urinalysis dipstick control. Kova Trol 1 is a dried human urine which is commercially available from ICL Scientific, Fountain Valley, Calif. In this test, the control solution was tested by adding to the reconstituted Kova Trol 1 vials and monitoring the urobilinogen values for both Ames N-Multistix ® SG and BMD Chemstrip ® 9 dipsticks by visual and instrument methods over a period of five days (controls were stored at 2°–8° C.). The urobilinogen was also quantitated by the $HgCl_2$ method (described hereinafter) and the tests were repeated at monthly intervals for stability testing of the urobilinogen additive at 2°–8° C. storage. Control urobilinogen values were positive over a five day period with a range of 4–8 mg/dl on day 1, with a slight decline of 2–4 mg/dl by day 5. All other dipstick analytes gave consistent results. It is concluded from this testing that the urobilinogen control solution of this invention provides a stable source of positive control for dipstick urobilinogens, which previously has not been available. Daily quality control of urine dipsticks can be performed in both the clinical laboratory and the doctor's office to minimize the possibility of reporting false negative results.

The $HgCl_2$ procedure for urinary urobilinogen determination mentioned above, is described by Rupe and Fetter, Clin. Chem. 27(8), 1385–1387 (1981). In this assay, urinary urobilinogen is oxidized to urobilinin with iodate in an acid medium, the pH is adjusted to 6 with sodium acetate, and the mixture is reacted with alcoholic $HgCl_2$ solution, extracted with $CHCl_3$, and measured spectrophotometrically at 513 nm. See also Watson, J. Biol. Chem. 200, 691–696 (1953).

The following detailed example will further illustrate the invention although it will be appreciated that the invention is not limited to this specific example or the specific details recited therein.

EXAMPLE

Preparation of sodium amalgam 5.4% sodium amalgam ($NaHg^{++}$) is prepared by cautiously adding 23 grams of freshly cut sodium metal in about pea size in small portions at a time to 400 grams of mercury in a beaker with stirring.

Preparation of urobilinogen concentrate

A diluent solution is prepared by admixing 2 ml of diethylamine with 40 ml of distilled water. To the diluent solution is added 2000 mg bilirubin and the solution allowed to mix on a magnetic stirrer for about 10–15 minutes in the dark by use of an amber colored reaction vessel. The resulting bilirubin solution (about 42 ml) is placed in a 200 ml brown bottle capable of being tightly sealed. About 100 gm of sodium amalgam, freshly washed off with deionized water, is added to the bilirubin solution. A magnetic stir bar is placed in the bottle which is then tightly sealed. The solution is stirred on a magnetic stirrer for about one hour. During this period, the solution changes from dark brown-black to a clear light yellow to orange color. After the one hour stirring period, the supernatant fluid which contains the urobilinogen solution is separated from the liquid mercury particles by pouring into a funnel containing glass wool and Whatman #1 filter paper. The filtered liquid is then dissolved in one half its volume of ethylene glycol such that the urobilinogen is contained in 33–$\frac{1}{3}$% glycol.

Due to the alkalinity of the above reaction, both from the diethylamine and the sodium hydroxide produced by the sodium amalgam breakdown with water, the pH is about 12.8–13.0. The pH thus is adjusted to about 8.3 by dropwise addition of concentrated HCl while stirring on the magnetic stirrer. The product is then stored at $-20°$ C. as a concentrated urobilinogen solution. The solution can be assayed as described herein and adjusted to obtain any desired urobilinogen content in the end product.

Preparation of urobilinogen diluent

To one liter of 5% ethylene glycol (950 ml water with 50 ml glycol) is added with stirring about one gm of bovine albumin. Alternatively, human albumin can be used in place of the bovine material. The solution is then buffered by addition of 12.1 gm TRIS (0.1 molar) and the pH adjusted to about 8.2 with 1 N HCl. To the buffered solution is then added with stirring about 150 mg of dithiothreitol and 1000 mg of disodium EDTA. Then about 5 mg fungizone, 50 mg of Vancomycin and 50 mg Gentimycin are added with mixing. The pH is again checked and adjusted to about 8.2. The final diluent product is stored at 5° C.

Preparation of urobilinogen control solution

About 0.3 ml of the above-prepared urobilinogen concentrate is mixed well with about 0.7 ml of the aboveprepared urobilinogen diluent to provide one ml of urobilinogen working solution which is adapted to develop about 4 mg/dl of urobilinogen by both chemical and dipstick tests in actual usage. The urobilinogen working solution (one ml) is added to a 5 ml volume amber colored glass ampule. Nitrogen gas is then used to purge air and oxygen from the ampule which is then sealed in a gas flame. Ampules thus sealed and stored at 5° C. retain urobilinogen stability for 18 months.

Urobilinogen assay system

A potassium iodate stock solution (0.2 mol/liter) is prepared by mixing 4.5 gm of $KIO_3$ in 100 ml distilled water. A potassium iodate working solution is prepared by adding one ml of the $KIO_3$ stock solution to 20 ml of acetic acid solution (2 mol/liter) which is prepared by adding 120 ml of glacial acetic acid to 800 ml distilled water and then diluting to 1000 ml.

A sodium acetate buffer solution, 2 mol/liter, pH 6.0, is prepared by adding 77.5 gm of sodium acetate to 350 ml of distilled water, adjusting to pH 6.0 with acetic acid, adding 5 gm of NaCl and diluting to 500 ml.

A mercuric chloride reagent is made by adding 10 gm $HgCl_2$ to 100 ml of absolute ethanol (100%).

The urobilinogen concentrate (10 $\mu l$) to be assayed is added to one ml distilled water in a test tube capable of holding 10–15 ml. Then 250 $\mu l$ of the above-prepared potassium iodate working solution, freshly made, is mixed with the urobilinogen concentrate and placed in the dark for about 20 minutes to allow the reaction to proceed to completion. One ml of the sodium acetate buffer is first added with mixing and then 0.5 ml of the mercuric chloride reagent also is added with mixing. After about ten minutes, during which period a secondary chemical reaction occurs, 5 ml of chloroform are added and mixed with a vortex mixer, whereby two phases result. The bottom layer (organic phase) is then separated and filtered through Whatman #1 filter paper into a clear test tube. The optical density, OD, (adsorbance) is measured at 513 nm and compared against a reagent blank. The number of mg/dl in the original ten $\mu l$ sample is calculated. This represents 100 $\mu l$ of addition to 10 ml of urine control media. The final urobilinogen concentrate can be adjusted to any desired OD for reproducible results.

Various other examples will be apparent to the person skilled in the art after reading the present disclosure without departing from the spirit and scope of the invention, and it is intended that all such other examples be included in the scope of the appended claims.

What is claimed is:

1. A stable control solution for the determination of urobilinogen comprising an aqueous solution of from about 3% to about 12% ethylene glycol, about 0.1% protein, and an amount of urobilinogen sufficient to develop upon dilution in use an activity of from about 0.1 to about 20 mg/dl urobilinogen, said composition being buffered to a pH of from about 8.0 to about 9.0 and retained in a hermetically sealed container under a blanket of inert gas.

2. The control solution of claim 1 in which the amount of urobilinogen is from about 40 to about 400 mg/dl.

3. The control solution of claim 2 in which the amount of ethylene glycol is about 8.0% the protein is albumin, and the pH is from about 8.2 to about 8.4.

4. The control solution of claim 3 in which the inert gas is nitrogen.

5. The control solution of claim 1 in which the amount of ethylene glycol is about 8.0%.

6. The control solution of claim 1 in which the protein is albumin.

7. The control solution of claim 1 in which the pH is from about 8.2 to about 8.4.

* * * * *